United States Patent [19]

Au

[11] 4,414,218
[45] Nov. 8, 1983

[54] CYANO-(SUBSTITUTED AND UNSUBSTITUTED PYRIDINYL) METHYL AND ARYL ESTERS OF CARBONIC ACID

[75] Inventor: Andrew T. Au, Needham, Mass.
[73] Assignee: The Dow Chemical Company, Midland, Mich.
[21] Appl. No.: 354,481
[22] Filed: Mar. 3, 1982
[51] Int. Cl.³ .................. C07D 213/55; A01N 43/40
[52] U.S. Cl. .............................. 424/263; 546/286; 546/287; 546/296; 546/300; 546/330
[58] Field of Search ............. 546/300, 330, 286, 287, 546/296; 424/263

[56] References Cited

U.S. PATENT DOCUMENTS

| | | | |
|---|---|---|---|
| 3,306,880 | 2/1967 | Lee et al. | 260/77.5 |
| 3,594,400 | 7/1971 | Boogaart et al. | 260/463 |
| 3,723,625 | 3/1973 | Boogaart et al. | 424/301 |
| 3,835,176 | 9/1974 | Matsuo et al. | 260/465 D |
| 4,247,475 | 1/1981 | Ching | 260/465 D |

FOREIGN PATENT DOCUMENTS 1217384  5/1966  Fed. Rep. of Germany .
1122658  8/1965  United Kingdom .

OTHER PUBLICATIONS

Uff et al., "Formation of Cyanohydrin Carbonates of Aromatic Aldehydes and Aryl Heteroaryl Ketones," *Synthetic Communications*, 8(3), 163–167 (1978).

*Primary Examiner*—Alan L. Rotman
*Attorney, Agent, or Firm*—Norman L. Sims; Douglas N. DeLine

[57] ABSTRACT

The novel compounds of this invention are pyridinyl cyano carbonates corresponding to the formula

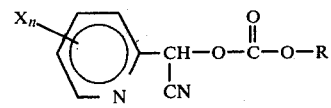

wherein:
R is alkyl or aryl of up to 20 carbons;
X is hydrogen, halo, cyano, nitro, R or OR; and
n is 1, 2, 3 or 4.

12 Claims, No Drawings

CYANO-(SUBSTITUTED AND UNSUBSTITUTED PYRIDINYL) METHYL AND ARYL ESTERS OF CARBONIC ACID

BACKGROUND OF THE INVENTION

Various alpha-cyano carbonates are disclosed in the literature. Alpha,alpha-(carbonyl-bis(oxy))bis-2-pyridineacetonitrile,

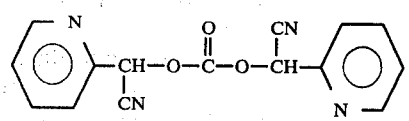

is taught in Gude German Pat. No. 1,217,384 assigned to H. Bernia-Chemie G.m.b.H., May 26, 1966, C.A. 65, 5374 (1966). Cyanophenylmethyl ethyl ester of carbonic acid and the method of preparing it is taught by Uff et al. in "Formation of Cyanohydrin Carbonates of Aromatic Aldehydes and Aryl Heteroaryl Ketones," *Synthetic Communications*, 8 (3), 163–167 (1978).

SUMMARY OF THE INVENTION

The novel compounds of this invention are pyridinyl cyano carbonates corresponding to the formula

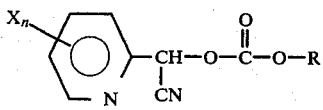

wherein:
R is alkyl or aryl of up to 20 carbons;
X is hydrogen, halo, cyano, nitro, R or OR; and
n is 1, 2, 3 or 4.
Preferably X is hydrogen, phenoxy, cyano or halo.

The novel compounds of this invention are oily liquids which are substantially insoluble in water, slightly soluble in nonpolar hydrocarbons, and substantially soluble in polar organic solvents. These compounds are useful in the control of fungal and bacterial pests.

Representative novel compounds coming within the scope of the present invention include the following: cyano-2-pyridinylmethyl ethyl ester of carbonic acid, cyano-2-pyridinylmethyl phenylmethyl ester of carbonic acid, cyano-(6-phenoxy-2-pyridinyl)methyl phenylmethyl ester of carbonic acid, and cyano-(6-phenoxy-2-pyridinyl)methyl ethyl ester of carbonic acid.

The pyridinyl cyano carbonates can be prepared in the following manner. An aldehyde having the formula

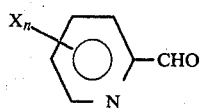

wherein X, n and R are as defined above, and a chloroformate are dissolved in a nonreactive water-immiscible organic solvent, such as methylene chloride. This solution is contacted with an aqueous solution of a metal cyanide, preferably an alkali or alkaline earth metal cyanide, such as sodium cyanide, and if desired, a catalyst such as a phase transfer "onium" salt, such as tetra-n-butylammonium chloride or benzyltrimethylammonium chloride in water. The mixture of these solutions is stirred for between about 1 hour and several days, preferably 3 to 6 hours. The product is recovered by washing, drying and concentrating the organic layer.

Between about 0.1 and 40.0 equivalents of chloroformate for each equivalent of aldehyde may be used, and between about 1.0 and 1.2 equivalents is preferred. Between about 1 and 20 equivalents of the metal cyanide per equivalent of aldehyde may be used, and between about 1.5 and 2.0 equivalents is preferred. The phase transfer catalyst is effective between about 0 and 10 equivalents per equivalent of aldehyde, and between about 0.01 and 0.1 equivalent is preferred. The reaction may be run either with or without a catalyst. The reaction may be run between about $-30°$ C. and $60°$ C., and between about $-10°$ C. and $25°$ C. is preferred.

DESCRIPTION OF SOME PREFERRED EMBODIMENTS

The following examples illustrate the present invention and the manner by which it can be produced, but as such, should not be construed as a limitation upon the overall scope of the invention.

EXAMPLE 1

To a stirred solution of 2.0 g of sodium cyanide in 10 ml of water and a catalytic amount of tetra-n-butylammonium chloride at $0°$ C. is added dropwise 30 ml of methylene chloride containing 2.14 g of 1-pyridine-carboxaldehyde and 2.2 g of ethylchloroformate. The mixture is stirred overnight while being warmed to room temperature. The organic layer is washed with water followed by a saturated bicarbonate solution, then dried over magnesium sulfate and concentrated to 2.81 g of a yellow oil giving a yield of 68 percent. Thin-layer chromatography, nuclear magnetic resonance spectroscopy and infrared spectroscopy all show that the product is cyano-2-pyridinylmethyl ethyl ester of carbonic acid.

EXAMPLE 2

To a stirred solution of 2.0 g of sodium cyanide in 10 ml of water and a catalytic amount of tetra-n-butylammonium chloride at $0°$ C. is added dropwise 30 ml of methylene chloride containing 2.14 g of 1-pyridine carboxaldehyde and 2.5 g of phenylmethylchloroformate. The mixture is stirred overnight while being warmed to room temperature. The organic layer is washed with water followed by a saturated bicarbonate solution, then dried over magnesium sulfate and concentrated to 2.21 g of a yellow oil giving a yield of 41 percent. Thin-layer chromatography, nuclear magnetic resonance spectroscopy and infrared spectroscopy all show that the product is cyano-2-pyridinylmethyl phenylmethyl ester of carbonic acid.

EXAMPLE 3

To a stirred solution of 2.0 g of sodium cyanide in 10 ml of water and a catalytic amount of tetra-n-butylammonium chloride at $0°$ C. is added dropwise 30 ml of methylene chloride containing 3.7 g of 6-phenoxy-1-pyridine carboxaldehyde and 3.5 g of phenylmethylchloroformate. The mixture is stirred overnight while being warmed to room temperature. The organic layer is washed with water followed by a saturated bicarbonate solution, then dried over magnesium sulfate and concentrated to 6.71 g of a yellow oil giving a yield of 92.7 percent. Thin-layer chromatography, nuclear magnetic resonance spectroscopy and infrared spectroscopy all show the product to be cyano-(6-phenoxy-2-pyridinyl)methyl phenylmethyl ester of carbonic acid.

EXAMPLE 4

To a stirred solution of 2.0 g of sodium cyanide in 10 ml of water and a catalytic amount of tetra-n-butylammonium chloride at 0° C. is added dropwise 30 ml of methylene chloride containing 3.7 g of 6-phenoxy-1-pyridine carboxaldehyde and 2.2 g of ethylchloroformate. The mixture is stirred overnight while being warmed to room temperature. The organic layer is washed with water followed by a saturated bicarbonate solution, then dried over magnesium sulfate and concentrated to 5.98 g of a yellow oil giving a yield of 91.7 percent. Thin-layer chromatography, nuclear magnetic resonance spectroscopy and infrared spectroscopy all show that the product is cyano-(6-phenoxy-2-pyridinyl)methyl ethyl ester of carbonic acid.

In accordance with the present invention, it has been found that the pyridinal cyano carbonates are useful as pesticides for the control of many bacterial and fungal pests. In addition, they can be applied to many plants and plant parts for fungal control without significant injury to the plants. Thus, they can be applied to the aerial portions of growing plants to control leaf-attacking fungal organisms and dispersed in the soil to control the root-attacking organisms.

The compounds can be employed as pesticides by distributing the compound in a pesticidally-effective quantity and usually in the form of a composition containing adjuvants (such as inert horticultural carriers) to aid in dispersing the same, so as to contact directly the organism to be controlled or, alternatively, so as to contact the growth medium or habitat of the organisms whereby eventual contact with such organisms will be established. For the control of bacterial and fungal pests, the active chemicals are applied in the form of compositions containing from 5 to 500 or more parts of the chemical per million parts by weight of the composition.

For such bactericidal, fungicidal and other pesticidal applications, the active compounds can be employed in an unmodified form or in the form of a liquid or finely divided solid composition. Thus, the compounds can be dispersed in a finely divided solid and employed as dusts. The compounds and such solid dispersions can also be dispersed in water with or without the aid of a surface active agent and the resulting aqueous suspensions employed as drenches or sprays. In other procedures, the compounds are employed as active constituents in solvent solutions, oil-in-water or water-in-oil emulsions or aqueous dispersions. The augmented compositions are adapted to be formulated as concentrates and subsequently diluted with additional liquid or solid adjuvants to produce the ultimate treating compositions.

The plants can be contacted by the active compounds at any stage of plant development employing one or more applications. The application of the active compounds to the plants can be by conventional techniques of foliar spraying, soil treatment or by seed or propagative root treatment.

The concentration of toxicant in liquid compositions generally is from about 0.0001 to 50 percent by weight. Concentrations up to 95 percent by weight are oftentimes conveniently employed, particularly in concentrate compositions. In dusts, the concentrations of the toxicant can be from about 0.1 to 95 percent by weight. In compositions to be employed as concentrates, the toxicants can be present in a concentration of from 5 to 98 percent by weight. For use as a spray, it is often convenient to prepare the compounds as wettable powders.

In representative operations, the compounds cyano-2-pyridinylmethyl phenylmethyl ester of carbonic acid and cyano-(6-phenoxy-2-pyridinyl)methyl phenylmethyl ester of carbonic acid were separately found to give at least 90 percent control of Fire Blight when employed as the sole toxicant in an aqueous treating composition of 400 parts per million by weight of the ultimate composition.

In other representative operations, the compounds cyano-2-pyridinylmethyl ethyl ester of carbonic acid and cyano-(6-phenoxy-2-pyridinyl)methyl ethyl ester of carbonic acid were found to give at least 90 percent control of Verticilium Wilt when employed separately as the sole toxicant in an aqueous treating composition at a concentration of 100 parts per million by weight of the ultimate composition.

When applied at a dosage level of from about 100 to 1000 parts per million, each of the compounds of the present invention, the utility of which is not specifically recited above, has the ability to kill, inhibit or otherwise control one or more of the aforementioned or other fungal or bacterial pests.

What is claimed is:

1. The pyridinyl cyano carbonates of the formula 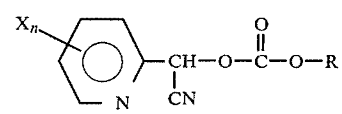 wherein:

R is alkyl of up to 20 carbons, phenyl or phenylmethyl;

X is hydrogen, halo, cyano, nitro, R or OR; and n is 1, 2, 3 or 4, with a proviso that n is 1 or 2 when X is cyano, nitro R or OR.

2. The compounds of claim 1 wherein X is hydrogen, phenoxy, cyano and halo.

3. A pesticidal composition comprising an inert horticultural carrier and as a pesticide, a compound of claim 1, the concentration of said pesticide being from 0.0001 to about 50 percent of the total weight of the composition.

4. A method for controlling Verticilium Wilt which comprises subjecting the Verticilium Wilt to an effective amount of the compound of claim 1.

5. A method for controlling fireblight which comprises subjecting the fireblight to an effective amount of the compound of claim 1.

6. A method for controlling Verticilium Wilt which comprises subjecting the Verticilium Wilt to an effective amount of the compound of claim 1.

7. A method for controlling fireblight which comprises subjecting the fireblight to an effective amount of the compound of claim 1.

8. The pyridinyl cyano carbonates of the formula

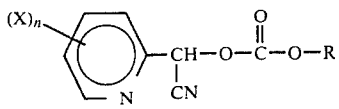

wherein:
R is $C_{1-20}$ alkyl, phenyl, or phenylmethyl;
X is hydrogen, phenoxy, cyano or halo; and
n is 1.

9. The compound as defined in claim 8 which is a cyano-2-pyridinylmethyl ethyl ester of carbonic acid.

10. The compound as defined in claim 8 which is a cyano-2-pyridinylmethyl phenylmethyl ester of carbonic acid.

11. The compound as defined in claim 8 which is a cyano-(6-phenoxy-2-pyridinyl)methyl ethyl ester of carbonic acid.

12. The compound as defined in claim 8 which is a cyano-(6-phenoxy-2-pyridinyl)methyl phenylmethyl ester of carbonic acid.

* * * * *